US006800639B2

(12) United States Patent
Giles et al.

(10) Patent No.: US 6,800,639 B2
(45) Date of Patent: Oct. 5, 2004

(54) PHARMACEUTICAL COMBINATION FOR THE TREATMENT OF CANCER

(75) Inventors: Francis Giles, Houston, TX (US); Hagpop Kantarjian, Houston, TX (US); Jacques Jolivet, Laval (CA)

(73) Assignee: Shire BioChem Inc., Laval (CA)

(*) Notice: Subject to any disclaimer, the term of this patent is extended or adjusted under 35 U.S.C. 154(b) by 0 days.

(21) Appl. No.: 10/104,067

(22) Filed: Mar. 25, 2002

(65) Prior Publication Data

US 2003/0083316 A1 May 1, 2003

Related U.S. Application Data

(60) Provisional application No. 60/277,975, filed on Mar. 23, 2001, and provisional application No. 60/330,601, filed on Oct. 25, 2001.

(51) Int. Cl.[7] .................. A61K 31/44; A61K 31/381; A61K 31/4355; A61K 31/4525; A61K 31/415
(52) U.S. Cl. .................. 514/300; 514/406; 514/220; 514/259.41; 514/317
(58) Field of Search ................ 514/81, 274, 86, 514/269, 34

(56) References Cited

U.S. PATENT DOCUMENTS

| 5,041,449 A | 8/1991 | Belleau et al. | |
|---|---|---|---|
| 5,270,315 A | 12/1993 | Belleau et al. | |
| 5,817,667 A | 10/1998 | Chu et al. | |
| 6,350,753 B1 | 2/2002 | Belleau et al. | |
| 6,630,480 B1 * | 10/2003 | Gourdeau et al. | 514/274 |
| 2002/0107225 A1 * | 8/2002 | Gourdeau et al. | 514/86 |

FOREIGN PATENT DOCUMENTS

| WO | WO 92/18517 | 10/1992 |
|---|---|---|
| WO | WO 9607413 | 3/1996 |
| WO | 96/07413 | 3/1996 |
| WO | 00/57861 | 10/2000 |
| WO | WO 00/57861 | 10/2000 |
| WO | WO 02/30922 | 4/2002 |

OTHER PUBLICATIONS

Salam A. Kadhim et al., "Potent Antitumor Activity of a Novel Nucleoside Analogue, BCH–4556 (Beta–L–Dioxolane–cytidine), in Human Renal Cell Carcinoma Xenograft Tumor Models", Cancer Research, American Association for Cancer Research, Baltimore, MD, US, vol. 57, No. 21, Nov. 1, 1997, pp. 4803–4810, XP000971188 ISSN: 0008–5472.

(List continued on next page.)

Primary Examiner—Frederick Krass
Assistant Examiner—Clinton Ostrup
(74) Attorney, Agent, or Firm—Millen, White, Zelano, Branigan, P.C.

(57) ABSTRACT

In accordance with the present invention there is provided a pharmaceutical combination useful for the treatment of cancer comprising at least one active compound of formula (I):

$$\underset{R}{\overset{O}{\diagdown}}\!\!\diagup\!\!\overset{O}{\diagdown}\!\!\!B \quad (I)$$

and at least one further therapeutic agent chosen from a nucleoside analogue and/or a chemotherapeutic agents; and, a method of treating a patient having cancer comprising at least one active compound of formula (I), as defined above, and at least one further therapeutic agent chosen from a nucleoside analogue and/or a chemotherapeutic agents.

26 Claims, 3 Drawing Sheets

OTHER PUBLICATIONS

Z. Yuzhu et al., "Homoharringtonine, cytarabine and aclarubicin (HAA) combination chemotherapy for acute myeloide leukemia (AML)", EMBASE, XP002192356, abstract.

Catharina J. A. Van Moorsel et al. "Gemcitabine: Future prospects of single agent and combination studies" Oncologist, Alphamed Press, US, vol. 2, No. 3, 1997, pp. 127–134, XP002110339, ISSN: 1083–7159 the whole document.

Database Biosis [Online] Biosciences Information Service, Philadelphia, PA, US; Nov. 16, 2001, Giles, Francis J. et al., "Troxatyl TM plus topotecan, ara–C, or idarubicin in patients (pts) with refractory acute myeloid leukemia (AML), myelodysplastic syndrome (MDS), or blastic–phase chronic myeloid leukemia (CML–BP): A randomized phase VII study.", Database accession No. PREV200200209956, XP002204436 abstract.

Database Biosis [Online] Biosciences Information Service, Philadelphia, PA, US; Nov. 16, 2001, Gourdeau Henriette et al., "Troxatyl TM overcomes cytarabine (ara–C) resistance in leukeic cells; Clinical and laboratory data.:", Database accession No. PREV200200250215 XP002204437 abstract.

Tohru Masaoka et al., "A phase II comparative study of idarubicin plus cytarabine versus daunorubicin plys cytarabine in adult acute myeloid leukemia.", Seminars in Hematology. United States Oct. 1996, vol. 33, No. 4 Suppl. 3, Oct. 10, 1996, pp. 12–17, XP001120118, ISSN: 0037–1963 the whole document.

Angelo M. Carella et al., "Idarubicin in combination with intermediate–dose cytarabine and VP–16 in the treatment of refractory or rapidly relapsed patients with acute myeloid leukemia. The GIMEMA Cooperative Group." Leukemia: Official Journal of the Leukemia Fund, U.K. England Feb. 1993, vol. 7, No. 2, Feb. 1993, pp. 196–199, XP001120113 ISSN: 0887–6924 the whole document.

Giorgio Lambertenghi–Deliliers et al., "Idarubicin plus cytarabine as first–treatment of acute nonlymphoblastic leukemia." Seminars in Oncology, United States Feb. 1989, vol. 16, No. 1 Suppl. 2, Feb. 1989, pp. 16–20, XP00900214 ISSN: 0093–7754 the whole document.

Gordeau et al., "Comparative study of a novel nucleoside analogue (Troxatyl, toxacitabine, BCH–4556) and AraC against leukemic human tumor xenografts expressing high or low cytidine deaminase activity", *Cancer Chemother Pharmocol*, 2001, pp. 236–240, vol. 47.

* cited by examiner

CalcuSyn Analysis of Troxacitabine/araC Combination on CCRF-CEM Cells.
(Experimental set up and example of results for a 72h continuous exposure)

PHARMACEUTICAL COMBINATION FOR THE TREATMENT OF CANCER

This application claims the benefit of U.S. Provisional Application Ser. No. 60/277,975 filed Mar. 23, 2001, and U.S. Provisional Application Ser. No. 60/330,601 filed Oct. 25, 2001, both of which are hereby incorporated in their entirety.

FIELD OF THE INVENTION

The present invention relates to pharmaceutical combinations useful in the treatment of cancer. Particularly, the combinations of this invention relate to dioxolane nucleosides with at least one further therapeutic agent chosen from nucleoside analogues and/or chemotherapeutic agents.

BACKGROUND OF THE INVENTION

Cancer is the second leading cause of death in the United States. It is estimated that cancer is responsible for 30% of all deaths in the Western world. Lung, colorectal, breast and prostate cancers are the four biggest killers.

Many nucleoside analogues have been found to possess anticancer activity. It was reported in (Weitman et al *Clinical Cancer Research* (2000), 6(4), pp 1574–1578 and Giles et al *Journal of Clinical Oncology* (2001), 19(3), pp 762–771 and also Gourdeau et al *Cancer Chemother. Pharmacol.* (2001), 47(3), pp 236–240) that troxacitabine (β-L-dioxolane cytidine, β-L-OddC, Troxatyl™), a nucleoside analogue, has shown to have potent activity in the treatment of various forms of cancers (e.g. solid tumours, adult leukemia and lymphomas).

Other important nucleoside analogues which are also well known in the treatment of cancer are Cytarabine (Ara-C), fludarabine, gemcitabine and cladribine. In the treatment of leukemia, combinations of cytarabine and anthracyclines have been the subject of most intense study. Despite improvements in the outcome of patients with current combination treatment programs, there exists a need to find other combinations of drugs which exhibit potent antitumor activity. In addition, the current therapies fail to cure most cancers once they have recurred.

The present invention provides combinations of troxacitabine with other nucleoside analogues and/or chemotherapeutic agents which exhibit potent antitumor activity and would greatly aid in the development of new combination therapy against cancer.

SUMMARY OF THE INVENTION

In one aspect, the present invention provides a novel pharmaceutical combination useful for the treatment of cancer in a mammal comprising at least one active compound of formula (1):

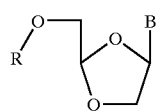

(I)

or a pharmaceutically acceptable salt thereof,
wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

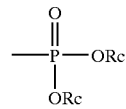

wherein each Rc is independently selected from the group comprising H, $C_{1-6}$ alkyl, $C_{2-6}$ alkenyl, $C_{2-6}$ alkynyl and a hydroxy protecting group;
and at least one further therapeutic agent chosen from nucleoside analogue and/or a chemotherapeutic agent.

The pharmaceutical combinations of the present invention are useful in cancer therapy, in particular in the treatment of cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, leukemia and lymphomas in patients.

In another aspect, the pharmaceutical combinations of the present invention are useful in cancer therapy, in particular in the treatment of cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, and lymphomas in patients.

In another aspect, the pharmaceutical combinations of the present invention are useful in cancer therapy, in particular in the treatment of leukemia.

In another aspect, the pharmaceutical combinations of the present invention are useful in cancer therapy, in particular in the treatment of pancreatic cancer.

In another aspect, there is provided a method of treating a patient having cancer comprising administering to said patient a therapeutically effective amount of a compound of formula (I) and at least one further therapeutic agent.

In another aspect, there is provided a method of treating a patient having cancer, in particular in the treatment of cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, leukemia and lymphomas, comprising administering to said patient a therapeutically effective amount of a compound of formula (I) and at least one further therapeutic agent.

In another aspect, there is provided a method of treating a patient having a cancer, in particular a cancer other than leukemia, comprising administering to said patient a therapeutically effective amount of a compound of formula (I) and at least one further therapeutic agent.

In another aspect, there is provided a method of treating a patient having cancer, in particular in the treatment of cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, and lymphomas, comprising administering to said patient a therapeutically effective amount of a compound of formula (I) and at least one further therapeutic agent.

In another aspect, there is provided a method of treating a patient having cancer, in particular in the treatment of refractory leukemia comprising administering to said patient having refractory leukemia a therapeutically effective amount of a compound of formula (I) and at least one further therapeutic agent. Preferably, the further therapeutic agent is other than doxorubicin. Also, the ratio of the compound of formula (I) to the further therapeutic agent is preferably 1:250 to 250:1, more preferably 1:50 to 50:1, especially 1:20 to 20:1.

In another aspect, there is provided a pharmaceutical formulation comprising the combination of the compound of formula (I) and at least one further therapeutic agent in combination with at least a pharmaceutically acceptable carrier or excipient. Preferably, the further therapeutic agent is other than doxorubicin. Also, the ratio of the compound of formula (I) to the further therapeutic agent is preferably 1:250 to 250:1, more preferably 1:50 to 50:1, especially 1:20 to 20:1.

Another aspect of the invention is the use of a compound according to formula (I) and at least one further therapeutic agent, for the manufacture of a medicament for treating cancer in a mammal. Preferably, the further therapeutic agent is other than doxorubicin. Also, the ratio of the compound of formula (I) to the further therapeutic agent is preferably 1:250 to 250:1, more preferably 1:50 to 50:1, especially 1:20 to 20:1.

DETAILED DESCRIPTION OF THE INVENTION

Figure 1:
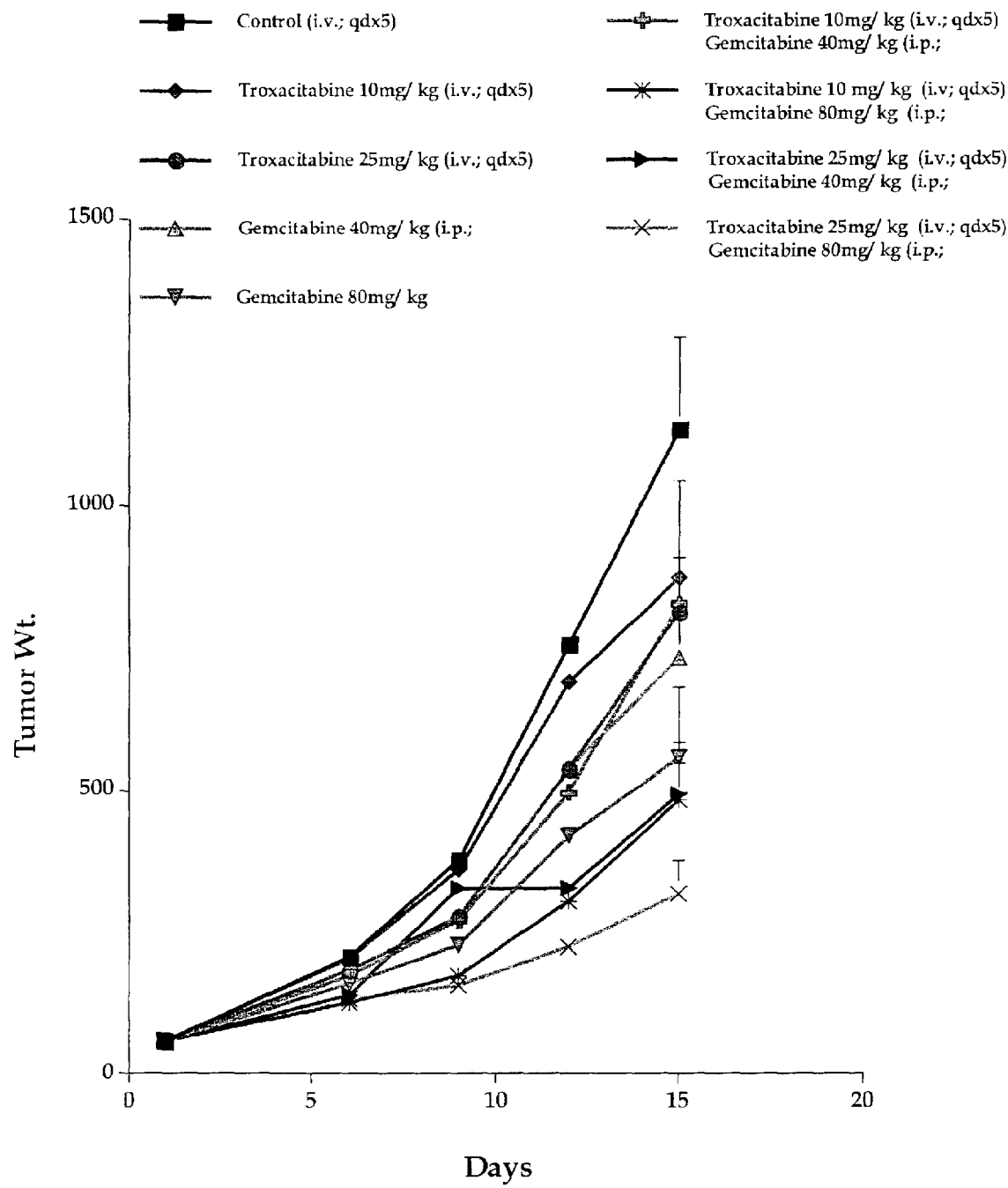
FIG. 1 represents the graphical representation of tumor growth inhibition results of single and combination dosing of troxacitabine and gemcitabine in the MiaPaCa Human pancreatic tumor xenograft model.

The present invention provides a novel pharmaceutical combination useful for the treatment of cancer in a mammal comprising at least one active compound of formula (I):

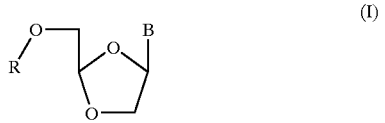
(I)

or a pharmaceutically acceptable salt thereof,
wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

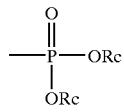

wherein each Rc is independently selected from the group comprising H, $C_{1-6}$ alkyl, $C_{2-6}$ alkenyl, $C_{2-6}$ alkynyl and a hydroxy protecting group;
and at least one further therapeutic agent chosen from a nucleoside analogue and/or a chemotherapeutic agent.

In one embodiment, R is H.
In one embodiment, B is cytosine.
In one embodiment, R is H and B is cytosine.
In one embodiment, B is 5-fluorocytosine.
In one embodiment, a compound of formula I is (−)-β-L-Dioxolane-Cytidine (β-L-OddC).

In one embodiment, a compound of formula I is (−)-β-Dioxolane-5-fluoro-Cytidine (5-FddC).

In another embodiment, the compounds of formula (I) of the present invention is substantially in the form of the (−) enantiomer.

In a further embodiment, the compounds formula (I) present in the pharmaceutical combination of the present invention are in the form of the (−) enantiomer at least 95% free of the corresponding (+) enantiomer.

In one embodiment, the compounds formula (I) present in the pharmaceutical combination of the present invention are in the form of the (−) enantiomer at least 97% free of the corresponding (+) enantiomer.

In one embodiment, the compounds formula (I) present in the pharmaceutical combination of the present invention are in the form of the (−) enantiomer at least 99% free of the corresponding (+) enantiomer.

It will be appreciated by those skilled in the art that the compounds of formula (I) contain at least two chiral centers. The compounds of formula (I) thus exist in the form of two different optical isomers (i.e. (+) or (−) enantiomers or β-L and β-D). All such enantiomers and mixtures thereof including racemic mixtures are included within the scope of the invention. The signal optical isomer or enantiomer can be obtained by method well known in the art, such as chiral HPLC, enzymatic resolution and chiral auxiliary. Alternatively, the enantiomers of the compounds of formula (I) can be synthesized by using optically active starting materials.

In one embodiment, the further therapeutic agent is a nucleoside analogue.

In one embodiment, the further therapeutic agent is a cytosine nucleoside analogue.

In one embodiment, the further therapeutic agent is a cytosine nucleoside analogue chosen from cytarabine or gemcitabine. Preferably, the ratio of the compound of formula (I) to the further therapeutic agent is 1:250 to 250:1, more preferably 1:50 to 50:1, especially 1:20 to 20:1.

In another embodiment, the further therapeutic agent is cytarabine. Preferably, the ratio of the compound of formula (I) to cytarabine is preferably 1:250 to 250:1, more preferably 1:50 to 50:1, especially 1:20 to 20:1.

In another embodiment, the further therapeutic agent is gemcitabine. Preferably, the ratio of the compound of formula (I) to gemcitabine is 1:250 to 250:1, more preferably 1:50 to 50:1, especially 1:20 to 20:1.

In one embodiment, the further therapeutic agent is a chemotherapeutic agent.

In another embodiment, the further therapeutic agent is idarubicin. Preferably, the ratio of the compound of formula (I) to idarubicin is preferably 1:250 to 250:1, more preferably 1:50 to 50:1, especially 1:20 to 20:1.

In one embodiment, at least one compound of formula (I) of the present invention is employed together with cytarabine, gemcitabine, idarubicin, or combinations thereof. Preferably, the ratio of the compound of formula (I) to the further therapeutic agent is preferably 1:250 to 250:1, more preferably 1:50 to 50:1, especially 1:20 to 20:1.

In another embodiment, the individual components of such combinations as defined above may be administered either sequentially or simultaneously in separate or combined pharmaceutical formulations.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

In one embodiment of the present invention, the compound of formula (I) present in the pharmaceutical combination of the present invention is (β-L-OddC) and at least one further therapeutic agent is chosen from cytarabine, gemcitabine and idarubicin. Preferably, the ratio of β-L-OddC to the further therapeutic agent is 1:250 to 250:1, more preferably 1:50 to 50:1, especially 1:20 to 20:1.

In one embodiment, the pharmaceutical combination of the present invention is a synergistic combination of therapeutic agents comprising β-L-OddC and at least one further therapeutic agent chosen from cytarabine, gemcitabine and idarubicin.

In one embodiment, the pharmaceutical combination of the present invention is β-L-OddC and cytarabine. Preferably, the ratio of β-L-OddC to cytarabine is 1:250 to 250:1, more preferably 1:50 to 50:1, especially 1:20 to 20:1.

In one embodiment, the pharmaceutical combination of the present invention is β-L-OddC and gemcitabine. Preferably, the ratio of β-L-OddC to gemcitabine is preferably 1:250 to 250:1, more preferably 1:50 to 50:1, especially 1:20 to 20:1.

In one embodiment, the pharmaceutical combination of the present invention is β-L-OddC and idarubicin. Preferably, the ratio of β-L-OddC to idarubicin is preferably 1:250 to 250:1, more preferably 1:50 to 50:1, especially 1:20 to 20:1.

In another embodiment, the present invention provides a combination for treating cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, leukemia and lymphomas in patients. Preferably, the further therapeutic agent is other than doxorubicin. Also, the ratio of the compound of formula (I) to the further therapeutic agent is preferably 1:250 to 250:1, more preferably 1:50 to 50:1, especially 1:20 to 20:1.

In another embodiment, the present invention provides a combination for treating cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, and lymphomas in patients. Preferably, the further therapeutic agent is other than doxorubicin. Also, the ratio of the compound of formula (I) to the further therapeutic agent is preferably 1:250 to 250:1, more preferably 1:50 to 50:1, especially 1:20 to 20:1.

In one embodiment, the present invention provides a combination as defined above for treating myelogenous leukemia, wherein the further therapeutic agent is preferably other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a combination as defined above for treating acute myelogenous leukemia, wherein the further therapeutic agent is preferably other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a combination as defined above for treating chronic myelogenous leukemia, wherein the further therapeutic agent is preferably other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a combination as defined above for treating refractory/relapsed leukemia, wherein the further therapeutic agent is preferably other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a combination as defined above for treating pancreatic cancer.

In another aspect, the present invention provides a method of treating a patient having cancer comprising administering to said patient a therapeutically effective amount of a compound of formula (I):

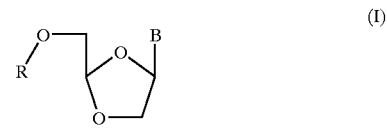

(I)

or a pharmaceutically acceptable salt thereof, wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

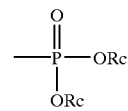

wherein each Rc is independently selected from the group comprising H, $C_{1-6}$ alkyl, $C_{2-6}$ alkenyl, $C_{2-6}$ alkynyl and a hydroxy protecting group;

and at least one further therapeutic agent chosen from a nucleoside analogue and/or a chemotherapeutic agent.

In another embodiment, there is provided a method of treating a patient having a cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, leukemia and lymphomas in patients. The ratio of the compound of formula (I) to the further therapeutic agent is preferably 1:250 to 250:1, more preferably 1:50 to 50:1, especially 1:20 to 20:1.

In another embodiment, there is provided a method of treating a patient having a cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, and lymphomas in patients.

In another embodiment, the present invention provides a method for treating myelogenous leukemia by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating acute myelogenous leukemia by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating chronic myelogenous leukemia by administering to the patient a therapeutically effective amount of a compound of formula (I) and at least one further therapeutic agent chosen from a nucleoside analogue and/or a chemotherapeutic agent Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating chronic myelogenous leukemia in blastic phase by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating refractory/relapsed leukemia by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating a patient who has refractory/relapsed leukemia and which has been previously treated with cytarabine by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating a patient who has refractory/relapsed leukemia and which has been previously treated with cytarabine and is resistant to cytarabine by administering to the patient a therapeutically effective amount of a compound of formula (I) and at least one further therapeutic agent chosen from a nucleoside analogue and/or a chemotherapeutic agent. Preferably, the further therapeutic agent is other than doxorubicin and the ratio of the compound of formula (I) to the further therapeutic agent is preferably 1:250 to 250:1, more preferably 1:50 to 50:1, especially 1:20 to 20:1.

In another embodiment, the present invention provides a method for treating a patient who has refractory/relapsed leukemia and which has been previously treated with cytarabine by administering to the patient β-L-OddC and cytarabine, wherein the ratio of β-L-OddC to cytarabine is preferably 1:250 to 250:1, more preferably 1:50 to 50:1, especially 1:20 to 20:1.

In another embodiment, the present invention provides a method for treating a patient with leukemia by administering to the patient β-L-OddC and at least one further therapeutic agent chosen from cytarabine, gemcitabine and idarubicin, wherein the ratio of β-L-OddC to the further therapeutic agent is preferably 1:250 to 250:1, more preferably 1:50 to 50:1, especially 1:20 to 20:1.

In another embodiment, the present invention provides a method for treating a patient with leukemia by administering to the patient a synergistic combination of β-L-OddC and at least one further therapeutic agent chosen from cytarabine, gemcitabine and idarubicin.

In another embodiment, the present invention provides a method for treating a patient with leukemia by administering to the patient β-L-OddC and cytarabine, wherein the ratio of β-L-OddC to cytarabine is preferably 1:250 to 250:1, more preferably 1:50 to 50:1, especially 1:20 to 20:1.

In another embodiment, the present invention provides a method for treating a patient with leukemia by administering to the patient β-L-OddC and gemcitabine, wherein the ratio of β-L-OddC to gemcitabine is preferably 1:250 to 250:1, more preferably 1:50 to 50:1, especially 1:20 to 20:1.

In another embodiment, the present invention provides a method for treating a patient with leukemia by administering to the patient β-L-OddC and idarubicin, wherein the ratio of β-L-OddC to idarubicin is preferably 1:250 to 250:1, more preferably 1:50 to 50:1, especially 1:20 to 20:1.

In another embodiment, the present invention provides a method for treating a patient with cancer by administering to the patient β-L-OddC and at least one further therapeutic agent chosen from cytarabine, gemcitabine and idarubicin, wherein the ratio of β-L-OddC to the further therapeutic agent is preferably 1:250 to 250:1, more preferably 1:50 to 50:1, especially 1:20 to 20:1.

In another embodiment, the present invention provides a method for treating a patient with cancer, in particular a cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, leukemia and lymphomas, by administering to the patient β-L-OddC and at least one further therapeutic agent chosen from cytarabine, gemcitabine and idarubicin, wherein the ratio of β-L-OddC to the further therapeutic agent is preferably 1:250 to 250:1, more preferably 1:50 to 50:1, especially 1:20 to 20:1.

In another embodiment, the present invention provides a method for treating a patient with cancer, other than leukemia, by administering to the patient β-L-OddC and at least one further therapeutic agent chosen from cytarabine, gemcitabine and idarubicin, wherein the ratio of β-L-OddC to the further therapeutic agent is preferably 1:250 to 250:1, more preferably 1:50 to 50:1, especially 1:20 to 20:1.

In another embodiment, the present invention provides a method for treating a patient with cancer, in particular a cancer selected from the group comprising lung cancer, prostate cancer, bladder cancer, colorectal cancer, pancreatic cancer, gastric cancer, breast cancer, ovarian cancer, soft tissue sarcoma, osteosarcoma, hepatocellular carcinoma, and lymphomas, by administering to the patient β-L-OddC and at least one further therapeutic agent chosen from cytarabine, gemcitabine and idarubicin, wherein the ratio of β-L-OddC to the further therapeutic agent is preferably 1:250 to 250:1, more preferably 1:50 to 50:1, especially 1:20 to 20:1.

In another embodiment, the present invention provides a method for treating a patient with cancer by administering to the patient a synergistic combination of β-L-OddC and at least one further therapeutic agent chosen from cytarabine, gemcitabine and idarubicin.

In another embodiment, the present invention provides a method for treating pancreatic cancer by administering to the patient a therapeutically effective amount of a compound of formula (I) and at least one further therapeutic agent chosen from a nucleoside analogue and/or a chemotherapeutic agent.

In another embodiment, the present invention provides a method for treating a patient with pancreatic cancer by administering to the patient β-L-OddC and gemcitabine.

There is also provided pharmaceutically acceptable salts of the compounds formula (I) present in the pharmaceutical combinations of the present invention. By the term pharmaceutically acceptable salts of compounds of general formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

References hereinafter to the pharmaceutical combinations according to the invention includes compounds of the general formula (I) or a pharmaceutically acceptable salt thereof.

Unless otherwise defined, all technical and scientific terms used herein have the same meaning as commonly understood by one of ordinary skill in the art to which this invention belongs. As used in this application, the term "leukemia" represents acute myelogenous leukemia or acute myeloid leukemia (AML), chronic myelogenous leukemia or chronic myeloid leukemia (CML), chronic lymphocytic leukemia (CLL), acute lymphocytic leukemia (ALL), hairy cell leukemia (HCL), myelodysplastic syndromes (MDS) or chronic myelogenous leukemia (CML-BP) in blastic and all subtypes of these leukemias which are defined by morphological, histochemical and immunological techniques that are well known by those of skill in the art.

The term "myelogenous leukemia" represent both acute and chronic myelogenous leukemias (AML, CML) which involve elements of the bone marrow (e.g. white cells, red cells and megakaryocytes) and includes all subtypes of these leukemias which are defined by morphological, histochemical and immunological techniques that are well known by those of skill in the art.

The terms "refractory/relapsed leukemia" represents previously treated patients which were either non responsive to treatment with chemotherapeutic agents or had a response to treatment and then relapsed.

The term "patient" is defined as any diseased human.

The term "alkyl" represents an unsubstituted or substituted (by a halogen, nitro, $CONH_2$, COOH, $O-C_{1-6}$ alkyl, $O-C_{2-6}$ alkenyl, $O-C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g., methyl, ethyl, n-propyl, isopropyl, butyl, pentyl, hexyl, fluorohexyl, cyclopropyl, cyclobutyl, cyclopentyl, or cyclohexyl).

The term alkyl is also meant to include alkyls in which one or more hydrogen atoms is replaced by an halogen, more preferably, the halogen is fluoro (e.g., $CF_3-$ or $CF_3CH_2-$).

The terms "alkenyl" and "alkynyl" represent an alkyl containing at least one unsaturated group (e.g., vinyl, 1-propenyl, allyl, 1-methylpropenyl, 2-butenyl, 2-butenyl, ethynyl, 1-propynyl, or 2-propynyl).

The term "aryl" represents an aromatic radical (e.g., phenyl and naphthyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

In one embodiment, the first compound of formula (I) is administered to the patient at a dose between about 1 mg/m² and about 8 mg/m²; the second therapeutic agent when cytarabine is administered to the patient at a dose between about 0.1 gm/m² and about 6 gm/M².

In another embodiment, the first compound of formula (I) is administered to the patient at a dose between about 1 mg/m² and about 8 mg/m²; the second therapeutic agent when gemcitabine is administered to the patient at a dose between about 0.1 gm/m² and about 6 gm/m².

In another embodiment, the first compound of formula (I) is administered to the patient at a dose between about 1 mg/m² and about 8 mg/m²; the second therapeutic agent when idarubicin is administered to the patient at a dose between about 1 mg/m² and about 30 gm/m².

In another embodiment, β-L-OddC is administered at 6mg/m² over 30 minutes per day on days 1 to 5 and cytarabine is administered at 1 gm/m² over 2 hours daily on days 1 to 5.

In another embodiment, β-L-OddC is administered a 5mg/m² over 30 minutes per day on days 1 to 5 and idarubicin is administered at 12 gm/m² over 2 hours daily on days 1 to 3.

It will be appreciated that the amount of pharmaceutical combination according to the invention required for use in treatment will vary not only with the particular compound selected but also with the route of administration, the nature of the condition for which treatment is required and the age and condition of the patient and will be ultimately at the discretion of the attendant physician. In general however, a suitable dose will be in a range of from about 0.1 to about 750 mg/kg of body weight per day, preferable in the range of 0.5 to 500 mg/kg/day, most preferably in the range of 1 to 300 mg/kg/day.

The desired dose may conveniently be presented in a single dose or as divided dose administered at appropriate intervals, for example as two, three, four or more doses per day.

The pharmaceutical combination according to the present invention is conveniently administered in unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5%. solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) or a pharmaceutically acceptable salts thereof is used in combination with a second therapeutic agent the dose of each compound may be either the same as or differ from that when the compound is used alone. Appropriate doses will be readily appreciated by those skilled in the art.

For advantageous effects of the combination of the compounds of formula (I) and the additional therapeutic agents, they may be administered over a wide ratio. In one embodiment, the ratio of the compounds of formula (I) to the additional therapeutic agents in the present invention is between 1:250 to 250:1. Preferably, the additional therapeutic agent is other than doxorubicin.

In one embodiment, the ratio of the compounds of formula (I) to the additional therapeutic agents in the present invention is between 1:50 to 50:1. Preferably, the additional therapeutic agent is other than doxorubicin.

In one embodiment, the ratio of the compounds of formula (I) to the additional therapeutic agents in our invention is between 1:20 to 20:1. Preferably, the additional therapeutic agent is other than doxorubicin. In a further embodiment, one may use from about 1:1 to about 1:15 of compounds of the invention:second therapeutic agent. In a further embodiment, one may use from about 1:1 to about 1:10 of compounds of the invention:second therapeutic agent. In a further embodiment, one may use from about 1:1 to about 1:5 of compounds of the invention:second therapeutic agent. In a further embodiment, one may use from about 1:1 to about 1:3 of compounds of the invention:second therapeutic agent. Preferably, the additional therapeutic agent is other than doxorubicin. If a further therapeutic agent is added, ratios will be adjusted accordingly.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical combination according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

The pharmaceutical combination according to the invention may also be formulated for direct administration to the Central Nervous System by intravenous administration. In addition, administration to the heart may be achieved.

For topical administration to the epidermis, the pharmaceutical combination according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredients in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compounds with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the pharmaceutical combination according to the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the pharmaceutical combination according to the present invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the pharmaceutical combination according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following examples are provided to illustrate various embodiments of the present invention and shall not be considered as limiting in scope. The compounds of formula (I), including but not limited to $\mu$-L OddC, were synthesized at Shire BioChem Inc. as previously described in PCT publication numbers WO96/07413A1, WO97/21706 and WO00/47759, all of which are hereby incorporated by reference.

The entire disclosures of all applications, patents and publications, cited above and below, are hereby incorporated by reference.

EXAMPLE 1

Evaluation of β-L OddC Alone in Patients with Refractory Leukemia

A study was conducted to investigate the activity of β-L OddC as a single agent in patients with refractory/relapsed leukemia. The study involved the treatment of patients with refractory or relapsed acute myeloid (AML) or lymphocytic (ALL) leukemia, myelodysplastic syndromes (MDS), or chronic myelogenous leukemia in blastic Phase (CML-BP). A total of 42 patients were treated in the study. As a result, a total of 39 patients were assessable for responses. As a result, 2 complete and 1 partial remmissions (18%) were observed in 16 evaluable AML patients.

EXAMPLE 2

Evaluation of β-L OddC in Combination with Ara-C

A study was conducted to define the safety and efficacy of β-L OddC given in combination with Ara-C in refractory/relapsed leukemia patients. The majority of the refractory patients in this study were previously treated with Ara-c. The study involved the treatment of patients with refractory acute myeloid leukemia (AML), myelodysplastic syndromes (MDS) or chronic myelogenous leukemia (CML-BP) in blastic phase disease using a combination of β-L OddC with Ara-C.

The initial doses of the combinations (Level 0) given to the patients were β-L OddC 5 mg/m$^2$ administered intravenously (IV) over 30 minutes per day for 5 consecutive days given with Ara-C 1 gm/m$^2$ administered IV over 2 hours daily days 1 through 5.

A total of 49 patients were registered in the study. The first two patients treated at Level 0 experienced Grade 3 skin rash. The next three were entered at Level −1 (4 mg/m$^2$ β-L OddC/0.75 gm/m$^2$ Ara-C) and had no skin rash. The protocol was then amended to permit dose re-escalation under prednisone prophylaxis. Thirteen additional patients were entered at Level 0 with prednisone. Two patients had Grade 3 rash and one a Grade 3 hand-foot syndrome following a second cycle of therapy. It was then decided to further escalate by increasing either the Ara-C or β-L OddC arm relative to Level 0 doses. Seven patients were entered at 5 mg/m$^2$ β-L OddC/1.25 gm/m$^2$ Ara-C and nineteen at 6 mg/m$^2$ β-L OddC/1 gm/m$^2$ Ara-C. Five patients were treated at 6 mg/m$^2$ β-L OddC/1.25 gm/m$^2$ Ara-C arm. The dose-limiting toxicity was liver transaminitis. Based on the results obtained, the suggested dose for further studies was determined to be β-L OddC 6 mg/m$^2$ administered IV over 30 minutes per day for 5 consecutive days given with ara-c at 1 gm/m$^2$ daily IV over 2 hours day 1 through 5 given with prednisone 25 mg daily.

The results were evaluated by the response criteria as follows: Complete Remission (CR) or Complete Remission without platelet recovery (CRp) and all other responses were considered as failures. CR means normalization of the peripheral blood and bone marrow with 5% or less blasts, normo- or hypercellular marrow, a granulocyte count of 1×10$^9$/L or above, and a platelet count of 100×10$^9$/L or above lasting for at least 4 weeks. CRp means as per CR but platelet count <100×10$^9$/L.

Seven patients had a CR (4 AML, 1 CML-BP and 2 MDS) and 4 patients had a CRp (4 AML). The results equate to a 22% (11/49) response rate achieved using the combination of β-L OddC with Ara-C. Based on the results obtained and comparison with the results of Example 1, it can be seen that a beneficial effect was obtained when the combination of β-L OddC with Ara-C was used in refractory/relapsed leukemia patients, including the patients who were previously treated with Ara-C.

EXAMPLE 3

Combination of β-L OddC and Ara-c in Leukemic Cell Lines CRRF-CEM

Figure 3:
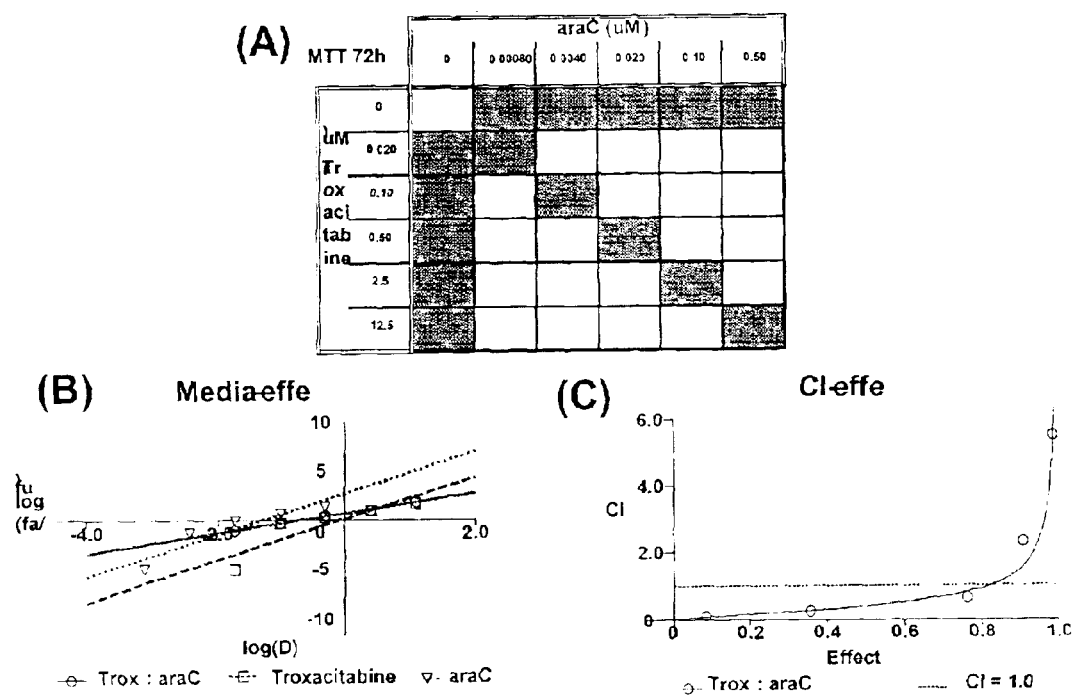
FIG. 3 represents the graphical results using CalcuSyn Analysis for the combination of troxacitabine and Ara-C as tested on the CCRF-CEM leukemia cell line.

The effect of the combination of β-L OddC and Ara-c on the survival of CRRF-CEM cells was measured using a standard MTT assay. This assay is based on the reduction of a tetrazolium compound to a soluble formazen derivative by the mitochondrial dehydrogenase enzymes of metabolically active and viable cells. The absorbance at 490 nm is directly proportional to the number of living cells in culture at a certain time point. In order to determine if the combination of β-L OddC and Ara-c was additive, antagonist or synergistic, the linear curve fitting (median-effect analysis; see FIG. 3) was used, using the CalcuSyn software (Biosoft, Ferguson, Mo.) which is based on algorithms developed by Chou and Talalay, *Adv. Enz. Regulation* 22, 1984, pp.27–55. Dose response curves were generated to determine the concentration that produced 50% of cell death ($IC_{50}$) at 2 hr and at 72 hr continuous exposures with the MTT assay being performed at 72 hr for both exposure times. Combinations of drugs were then generated around the $IC_{50}$'s of each drug to allow a constant ratio in order to determine if the combination was additive, synergistic or antagonistic. Combination indices (CI's) were generated from the CalcuSyn software for each combination, in triplicate, using the results obtained from each drug alone and their effect in combination within the same experiment (see Table 1). A CI below 1 is an indication of synergy, while a CI equal to 1 represents additivity, and a CI above 1 indicates antagonism.

TABLE 1

CalcuSyn Analysis (CI) of the Cytotoxic Effect of
Troxacitabine/araC Combination on CCRF-CEM Cells.

| Troxacitabine | | araC | | Trox/araC (2:1) | | |
|---|---|---|---|---|---|---|
| (nM) | % Toxicity | (nM) | % Toxicity | (nM) | % Toxicity | CI* |

(A) 2 h

| | | | | | | |
|---|---|---|---|---|---|---|
| 31 | 3 ± 3 | 15 | 15 ± 8 | 31/15 | 31 ± 9 | 0.71 ± 0.08 |
| 62 | 12 ± 7 | 31 | 38 ± 11 | 62/31 | 47 ± 11 | 0.72 ± 0.09 |
| 125 | 11 ± 2 | 62 | 61 ± 10 | 125/62 | 70 ± 13 | 0.59 ± 0.16 |
| 250 | 24 ± 3 | 125 | 78 ± 6 | 250/125 | 85 ± 7 | 0.52 ± 0.10 |
| 500 | 34 ± 6 | 250 | 88 ± 4 | 500/250 | 92 ± 4 | 0.55 ± 0.09 |

| Troxacitabine | | araC | | Trox/araC (25:1) | | |
|---|---|---|---|---|---|---|
| (nM) | % Toxicity | (nM) | % Toxicity | (nM) | % Toxicity | CI |

(B) 72 h

| | | | | | | |
|---|---|---|---|---|---|---|
| 20 | 0 | 0.8 | 1 ± 2 | 20/0.8 | 9 ± 7 | 0.2 ± 0.1 |
| 100 | 28 ± 5 | 4 | 13 ± 7 | 100/4 | 43 ± 6 | 0.3 ± 0.1 |
| 500 | 65 ± 2 | 20 | 50 ± 5 | 500/20 | 78 ± 2 | 0.7 ± 0.1 |
| 2500 | 90 ± 2 | 100 | 85 ± 2 | 2500/100 | 92 ± 2 | 2.1 ± 0.2 |
| 12500 | 98 ± 1 | 500 | 97 ± 2 | 12500/500 | 98 ± 1 | 6.0 ± 0.8 | n = 3 in triplicate
*CI: Combination Index (CI < 1 indicates synergy; CI = 1 indicates additivity; and CI > 1 indicates antagonism)

EXAMPLE 4
Evaluation of β-L OddC in Combination with Idarubicin

A study was conducted to define the safety and efficacy of β-L OddC given in combination with idarubicin in refractory leukemia patients. The study involved the treatment of patients with refractory acute myeloid leukemia (AML), myelodysplastic syndromes (MDS) or chronic myelogenous leukemia (CML-BP) in blastic phase disease disease using a combination of β-L OddC with idarubicin.

The initial doses of the combinations (Level 0) were β-L OddC 5 mg/m² administered IV over 30 minutes per day for 5 consecutive days given with idarubicin 12 mg/m² daily by rapid (1 to 5 minute) IV infusion on days 1 through 3.

A total of 20 patients were registered in the study. Two of the four patients treated at Level 0 experienced Grade 3 mucositis. One of these two patients also had a Grade 3 hand-foot syndrome. Sixteen patients were entered at Level −1 (4 mg/m² β-L OddC/9 mg/m² idarubicin). Two of these patients had serious adverse events (SAEs): one had a GI bleed and another one had an episode of hepatotoxicity. There were two CRs in 16 patients with AML, one Cr in two MDS patients and one in two CML-BP patients. Based on the results obtained the recommended dose for further studies was determined to be Level −1.

EXAMPLE 5
Evaluation of β-L OddC in Combination with Gemcitabine

In vivo studies were evaluated using β-L OddC in combination with gemcitabine. The MiaPaCa and Panc-01 human pancreatic tumor xenograft models were used in these studies as follows:

(i) Method Used in Evaluating Troxacitabine±Gemcitabine vs. MiaPaCa Human Pancreatic Tumor Xenograft Female nude mice weighing approximately 20 g were implanted s.c. by trocar with fragments of human tumor harvested from s.c. growing tumors in nude mice hosts. When the tumors were approximately 58mg in size (12 days following inoculation), the animals were pair-matched into treatment and control groups. Each group contained 10 mice, each of which was ear-tagged and followed individually throughout the experiment. Initial doses were given on Day 1 following pair matching. Troxacitabine was administered intravenously at 10 mg/kg and 25 mg/kg on a qd×5 schedule. Gemcitabine (Eli Lilly, Lot# 4MT16M) was administered intraperitoneally at 40 mg/kg and 80 mg/kg on a q3d×4 schedule. In addition, troxacitabine and gemcitabine were administered together in a series of combinations using the same route, doses and schedule.

Mice were weighed twice weekly, and tumor measurements were taken by calipers twice weekly, starting on Day 1. These tumor measurements were converted to mg tumor weight by a well-known formula, $(W^2 \times L)/2$. The experiment was terminated when the control group tumor size reached an average of 1 gram. Upon termination, the mice were weighed, sacrificed and their tumors were excised. The tumors were weighed, and the mean tumor weight per group was calculated. In these models, the change in mean treated tumor weight/the change in mean control tumor weight×100 (ΔT/ΔC) was subtracted from 100% to give the tumor growth inhibition (TGI) for each group.

Some drugs may cause tumor shrinkage in these tumor enograft models. With these agents, the final weight of a given tumor is subtracted from its own weight at the start of treatment on Day 1. This difference, divided by the initial tumor weight, is converted to percent shrinkage. The mean percent tumor shrinkage can be calculated from data from the mice in a group that experienced tumor regressions. If the tumor completely disappears in a mouse, it is considered a complete regression or complete tumor shrinkage.

(ii) Panc.−01 Human Pancreatic Tumor Xenograft

The similar method as previously described in (i) was used for the evaluation of Troxacitabine±Gemcitabine vs. Panc.−01 Human Pancreatic tumor xenograft.

(iii) Determination of Maximum Tolerated Dose (MTD)

Preliminary studies were conducted to determine MTD for troxacitabine and of the troxacitabine/gemcitabine combination. Troxacitabine was administered i.v. on a qd×5 schedule to non-tumored female nude mice. At a dose of 10 mg/kg, there were no deaths or weight loss. At a dose of 25 mg/kg, there were no deaths, but there was an average weight loss of one percent on Day 5. Weight gain thereafter until the end of the protocol on Day 23 indicated that the maximum tolerated doase is greater than 25 mg/kg on the qd×5 schedule.

Combinations of troxacitabine and gemcitabine were tested in four groups of mice using 10 and 25 mg/kg of troxacitabine (route and schedule as tested above) with 40 and 80 mg/kg of gemcitabine administered i.p. on a q3d×4 schedule. The combination of 10 mg/kg troxacitabine and 40 mg/kg gemcitabine produced no deaths, but there was weight loss of 6 percent on Day 5 and no weight gain until Day 12. The 10 mg/kg troxacitabine and 80 mg/kg gemcitabine combination actually had less weight loss (4.8 percent on Day 5) with a more rapid return to weight gain. Combination of 25 mg/kg troxacitabine and 40 mg/kg gemcitabine caused 5.6 percent weight loss on Day 5, while the highest dose combination, 25 mg/kg troxacitabine and 80 mg/kg gemcitabine, produced less at 4 percent on Day 5. All dose groups rapidly recovered from their weight loss.

Table 2 represents tumor growth inhibition results of single and combination dosing of troxacitabine and gemcitabine against the MiaPaCa Human pancreatic tumor xenograft model. Graphical representation of the results is shown in FIG. 1.

Figure 2:
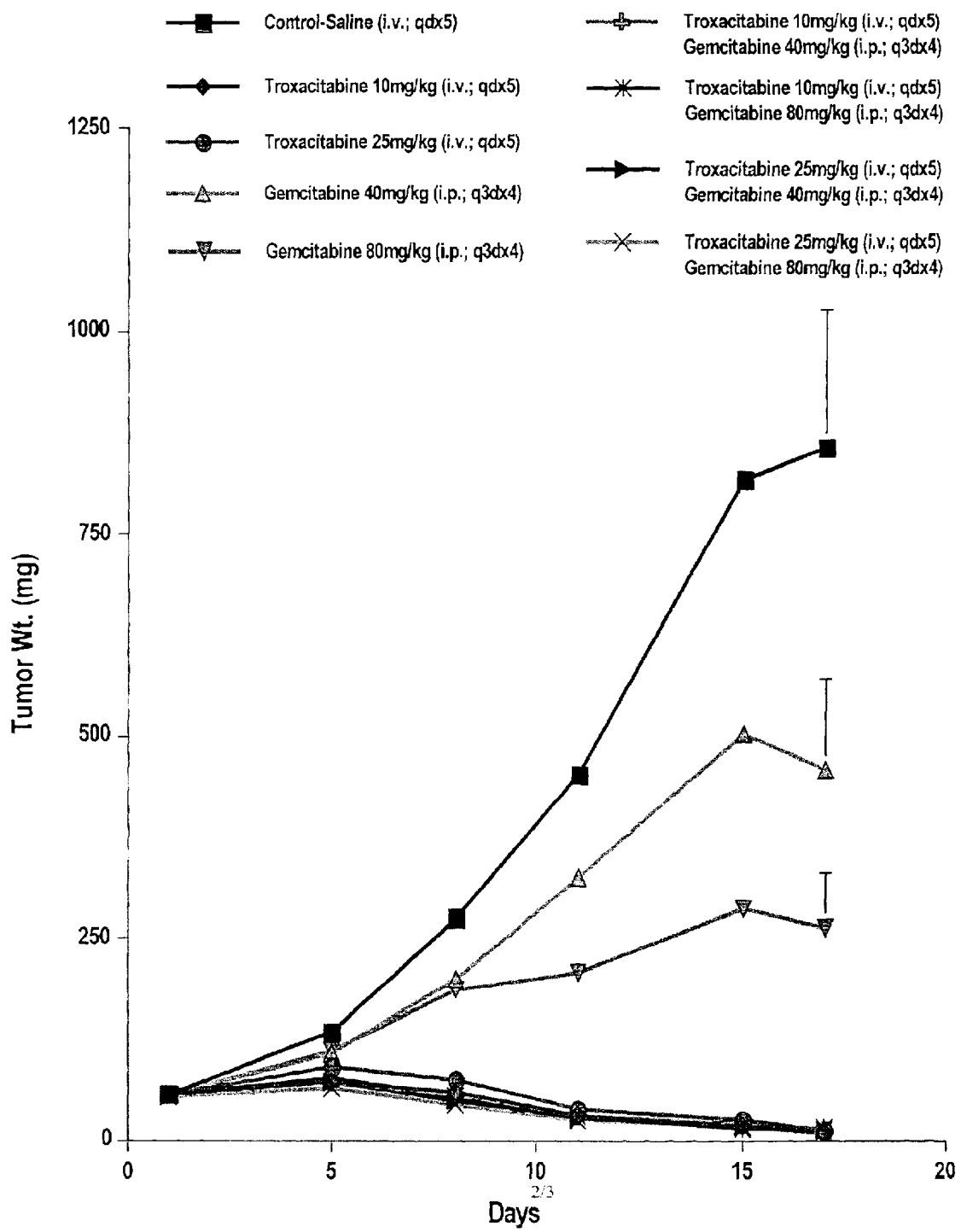
FIG. 2 represents the graphical representation of tumor growth inhibition results of single and combination dosing of troxacitabine and gemcitabine in the Panc-01 Human pancreatic tumor xenograft model.

Table 3 represents tumor growth inhibition results of single and combination dosing of troxacitabine and gemcitabine against the Panc-1 Human pancreatic tumor xenograft model. Graphical representation of the results is shown in FIG. 2.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

TABLE 2

Troxacitabine ± Gemcitabine vs. MiaPaCa Human Pancreatic Tumor Xenograft Model

| Group | n | Dose (mg/kg) | Route & Schedule | Weight Change (Day 6) | Weight Change (Day 12) | Final Tumor Wt. (Mean ± SEM) | % Tumor Growth Inhibition | Mice with Partial Shrinkage | Mice with Complete Shrinkage | # of Toxic Deaths |
|---|---|---|---|---|---|---|---|---|---|---|
| Control | (10) | — | i.v.; qd × 5 | +2.6% | +2.8% | 1133.4 ± 159.1 | — | 0 | 0 | 2 |
| Troxactabine[1] | (10) | 10 | i.v.; qd × 5 | +0.2% | +3.0% | 872.7 ± 171.1 | 23.9% | 0 | 0 | 3 |
| Troxactabine[1] | (10) | 25 | i.v.; qd × 5 | −3.9% | +8.0% | 813.4 ± 57.9 | 29.7% | 0 | 0 | 0 |
| Gemcitabine[2] | (10) | 40 | i.p.; q3d × 4 | −1.6% | +3.2% | 733.0 ± 98.7 | 37.3% | 0 | 0 | 0 |
| Gemcitabine[2] | (10) | 80 | i.p.; q3d × 4 | −1.0% | +2.8% | 553.8 ± 124.3 | 53.6% | 0 | 0 | 1 |
| Troxacitabine[1] Gemcitabine[2] | (10) | 10 40 | i.v.; qd × 5 i.p.; q3d × 4 | −6.0% | +3.5% | 826.5 ± 81.8 | 28.5% | 0 | 0 | 0 |
| Troxacitabine[1] Gemcitabine[2] | (10) | 10 80 | i.v.; qd × 5 i.p.; q3d × 4 | −9.8% | −2.9% | 483.4 ± 97.5 | 60.0% | 0 | 0 | 1 |
| Troxacitabine[1] Gemcitabine[2] | (10) | 25 40 | i.v.; qd × 5 i.p.; q3d × 4 | −8.4% | +2.4% | 492.3 ± 52.3 | 59.7% | 0 | 0 | 0 |
| Troxacitabine[1] Gemcitabine[2] | (10) | 25 80 | i.v.; qd × 5 i.p.; q3d × 4 | −9.7% | −16.4% | 316.3 ± 58.7 | 76.3% | 0 | 0 | 3 |

Note: The control and vehicle for Troxacitabine was saline.
[1]BioChem Pharma, Lot# 23g1-AL-2P.
[2]Eli Lilly, Lot# 4MT16M.

TABLE 3

Troxacitabine ± Gemcitabine vs. Panc-01 Human Pancreatic Tumor Xenograft

| Group (n = 10) | Dose (mg/kg) | Route & Schedule | Weight Change (Day 8) | Weight Change (Day 17) | Final Tumor Wt. (Mean ± SEM) | % Tumor Growth Inhibition | Mice with Partial Shrinkage | Mean % Tumor Shrinkage | Mice with Complete Deaths |
|---|---|---|---|---|---|---|---|---|---|
| Control | Saline | i.v.; qd × 5 | +0.7% | +7.9% | 855.9 ± 170.7 | — | 0 | — | 0 0 |
| Troxacitabine[1] | 10 | 10 i.v.; qd × 5 | +0.3% | +11.7% | 11.1 ± 2.1 | — | 9 | 77.5% | 1 0 |
| Troxacitabine[1] | 25 | iv.; qd × 5 | −2.1% | +11.1% | 12.5 ± 1.9 | — | 9 | 72.6% | 1 0 |
| Gemcitabine[2] | 40 | i.p.; q3d × 4 | +1.4% | +13.0% | 457.8 ± 113.9 | 49.8% | 0 | — | 0 0 |
| Gemcitabine[2] | 80 | i.p.; q3d × 4 | −1.7% | +15.9% | 262.2 ± 67.7 | 74.3% | 0 | — | 0 0 |
| Troxacitabine[1] Gemcitabine[2] | 10 40 | i.v.; qd × 5 i.p.; q3d × 4 | −7.1% | +6.8% | 13.2 ± 1.1 | — | 10 | 73.9% | 0 0 |
| Troxacitabine[1] Gemcitabine[2] | 10 80 | iv.; qd × 5 i.p.; q3d × 4 | −5.8% | +9.1% | 14.6 ± 0.8 | — | 10 | 70.1% | 0 0 |
| Troxacitabine[1] Gemcitabine[2] | 25 40 | i.v.; qd × 5 i.p.; q3d × 4 | −8.4% | +8.5% | 12.4 ± 1.2 | — | 10 | 76.3% | 0 0 |
| Troxacitabine[1] Gemcitabine[2] | 25 80 | i.v.; qd × 5 i.p.; q3d × 4 | −15.4% | +4.1% | 14.0 ± 1.4 | — | 9 | 73.1% | 0 1 |

Note: The control and vehicle for Troxacitabine was saline.
[1]BioChem Pharma, Lot# 23g1-AL-2P.
[2]Eli Lilly, Lot# 4MT16M.

What is claimed is:

1. A pharmaceutical combination comprising at least one active compound of formula (I):

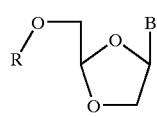
(I)

or a pharmaceutically acceptable salt thereof,
wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

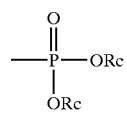

wherein each Rc is independently selected from the group comprising H, $C_{1-6}$ alkyl, $C_{2-6}$ alkenyl, $C_{2-6}$ alkynyl and a hydroxy protecting group; and
gemcitabine and the ratio of the compound of formula (I) to gemcitabine is 1:250 to 250:1.

2. The pharmaceutical combination according to claim 1 wherein R is H.

3. The pharmaceutical combination according to claim 1 wherein B is cytosine.

4. The pharmaceutical combination according to claim 1 wherein R is H and B is cytosine.

5. The pharmaceutical combination according to claim 1 wherein B is 5-fluorocytosine.

6. The pharmaceutical combination according to claim 1, wherein a compound of formula I is (−)-β-L-Dioxolane-Cytidine (β-L-OddC).

7. The pharmaceutical combination according to claim 1, wherein a compound of formula I is (−)-β-Dioxolane-5-fluoro-Cytidine (5-FddC).

8. The pharmaceutical combination according to claim 1, wherein the compound of formula I is substantially in the form of the (−) enantiomer.

9. The pharmaceutical combination according to claim 1 wherein said compound of formula (I) is at least 97% free of the corresponding (+) enantiomer.

10. A pharmaceutical combination according to claim 1, wherein the compound of formula (I) and gemcitabine are present in a ratio between about 1:50 to about 50:1.

11. A pharmaceutical combination according to claim 1, wherein the compound of formula (I) and gemcitabine are present in a ratio between about 1:20 to about 20:1.

12. A pharmaceutical combination according to claim 1, wherein gemcitabine and the compound of formula (I) are in separate pharmaceutical formulations.

13. A pharmaceutical composition comprising a pharmaceutical combination according to claim 1 and at least one pharmaceutically acceptable carrier or excipient.

14. A composition according to claim 13, wherein the compound of formula (I) is at least 97% free of the corresponding (+) enantiomer.

15. A composition according to claim 13, wherein the active compound and the other therapeutic agents are present in a synergistic ratio.

16. A pharmaceutical combination comprising

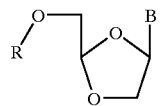
(I)

or a pharmaceutically acceptable salt thereof,
wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

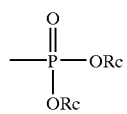

wherein each Rc is independently selected from the group comprising H, $C_{1-6}$ alkyl, $C_{2-6}$ alkenyl, $C_{2-6}$ alkynyl and a hydroxy protecting group; and
gemcitabine at least one further therapeutic agent chosen from a nucleoside analogue and/or a chemotherapeutic agent, wherein the compound of formula (I) and gemcitabine are present in a synergistic ratio.

17. A method of treating a patient having pancreatic cancer, comprising administering to said patient a therapeutically effective amount of a compound of formula I:

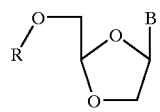
(I)

or a pharmaceutically acceptable salt thereof,
wherein B is cytosine or 5-fluorocytosine and R is selected from the group comprising H,

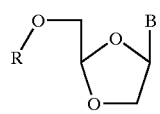
(I)

or a pharmaceutically acceptable salt thereof,
wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

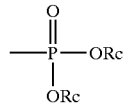

wherein each Rc is independently selected from the group comprising H, $C_{1-6}$ alkyl, $C_{2-6}$ alkenyl, $C_{2-6}$ alkynyl and a hydroxy protecting group; and
gemcitabine, wherein the ratio of the compound of formula (I) to gemcitbine is 1:250 to 250:1.

18. The method according to claim 17, wherein said patient is administered a therapeutically effective amount of β-L-OddC and Gemcitabine.

19. The method according to claim 17, wherein R is H and B is cytosine.

20. The method according to claim 17, wherein the β-L-dioxolane is at least 97% free of the corresponding (+) enantiomer.

21. The method according to claim 17, wherein the compounds of formula (I) and the further therapeutic agents are administered to said patient in need thereof sequentially.

22. The method according to claim 17, wherein the compounds of formula (I) and the other therapeutic agents are administered to said patient in need thereof simultaneously.

23. The method according to claim 17, wherein the active compound and the therapeutic agents are present in a synergistic ratio.

24. The method according to claim 17, wherein the active compound and the therapeutic agents are present in a ratio between about 1:50 to about 50:1.

25. The method according to claim 17, wherein the active compound and the therapeutic agents are present in a ratio between about 1:20 to about 20:1.

26. A method according to claim 17, wherein said compound of formula (I) is administered at a dose of between 1 mg/m$^2$ and 8 mg/m$^2$, and gemcitabine is administered at a dose of between 0.1 gm/m$^2$ and 6 gm/m$^2$.

* * * * *

UNITED STATES PATENT AND TRADEMARK OFFICE
CERTIFICATE OF CORRECTION

PATENT NO. : 6,800,639 B2
DATED : October 5, 2004
INVENTOR(S) : Francis Giles et al.

It is certified that error appears in the above-identified patent and that said Letters Patent is hereby corrected as shown below:

<u>Column 20,</u>
Line 1, "comprising" should read -- comprising at least one active compound of formula (I): --.
Lines 24-26, delete "at least one further therapeutic agent chosen from a nucleoside analogue and/or a chemotherapeutic agent --.
Lines 38-49, delete the lines in their entirety.
Line 64, "gemcitbine" should read -- (I) to gemcitabine --.

Signed and Sealed this

Twenty-eighth Day of June, 2005

JON W. DUDAS
*Director of the United States Patent and Trademark Office*